(12) United States Patent
Culp et al.

(10) Patent No.: US 7,435,703 B2
(45) Date of Patent: Oct. 14, 2008

(54) CATALYST COMPRISING IRON OXIDE MADE BY HEAT DECOMPOSITION OF AN IRON HALIDE AND A LANTHANIDE

(75) Inventors: Robert Dielman Culp, Katy, TX (US); Eugene Harry Theobald, Richmond, TX (US); Sarah Louise Weaver, Covington, LA (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 10/352,819

(22) Filed: Jan. 28, 2003

(65) Prior Publication Data

US 2003/0144566 A1 Jul. 31, 2003

Related U.S. Application Data

(60) Provisional application No. 60/353,586, filed on Jan. 30, 2002.

(51) Int. Cl.
*B01J 23/00* (2006.01)
(52) U.S. Cl. .................. 502/302; 502/303; 502/304
(58) Field of Classification Search ............... 502/302, 502/304, 305, 303
See application file for complete search history.

(56) References Cited

U.S. PATENT DOCUMENTS

| | | | | |
|---|---|---|---|---|
| 1,368,748 A | | 2/1921 | Penniman, Jr. | |
| 4,749,674 A | * | 6/1988 | Dejaifve et al. | 502/304 |
| 4,822,936 A | | 4/1989 | Maurer et al. | 585/259 |
| 5,023,225 A | * | 6/1991 | Williams et al. | 502/304 |
| 5,156,816 A | | 10/1992 | Butler et al. | 422/141 |
| 5,171,914 A | | 12/1992 | Hamilton, Jr. | 585/444 |
| 5,190,906 A | | 3/1993 | Murakami et al. | 502/304 |
| 5,401,485 A | | 3/1995 | Hamilton, Jr. | 423/632 |
| 5,504,268 A | | 4/1996 | van der Aalst et al. | 585/259 |
| 5,597,547 A | | 1/1997 | Hamilton, Jr. | 423/632 |
| 5,668,075 A | | 9/1997 | Milam et al. | 502/338 |
| 5,689,023 A | | 11/1997 | Hamilton, Jr. | 585/444 |
| 5,824,831 A | * | 10/1998 | Shiraki et al. | 585/444 |
| 5,911,967 A | | 6/1999 | Ruthner | 423/632 |
| 6,166,280 A | * | 12/2000 | Rubin et al. | 585/445 |
| 6,184,174 B1 | * | 2/2001 | Rubini et al. | 502/304 |
| 6,191,065 B1 | | 2/2001 | Williams et al. | 502/300 |
| 6,465,704 B2 | * | 10/2002 | Williams et al. | 585/444 |
| 6,551,958 B1 | * | 4/2003 | Baier et al. | 502/304 |

FOREIGN PATENT DOCUMENTS

| | | | |
|---|---|---|---|
| EP | 850881 | * | 7/1998 |
| EP | 0894528 A2 | | 2/1999 |
| EP | 1027928 A1 | | 8/2000 |
| EP | 1471999 | | 3/2007 |
| WO | WO 02/083569 | | 10/2002 |

OTHER PUBLICATIONS

Grant & Hackh's Chemical Dictionary, 5$^{th}$ edition, 1987, p. 348.*

* cited by examiner

*Primary Examiner*—Steven Bos

(57) ABSTRACT

A catalyst which is based upon an iron oxide and a compound of a lanthanide, of which iron oxide at least a portion is made by a process which involves heat decomposition of an iron halide, the lanthanide being in a quantity in the range of from 0.07 to 0.15 mole per mole iron oxide present in the catalyst, calculated as $Fe_2O_3$; a process for the preparation of the catalyst; a process for the dehydrogenation of an alkylaromatic compound which process involves contacting a feed containing the alkylaromatic compound with the catalyst; and a method of using an alkenylaromatic compound for making polymers or copolymers, in which method the alkenylaromatic compound has been prepared by the dehydrogenation process.

40 Claims, No Drawings

CATALYST COMPRISING IRON OXIDE MADE BY HEAT DECOMPOSITION OF AN IRON HALIDE AND A LANTHANIDE

This application claims the benefit of U.S. Provisional Application No. 60/353,586 filed Jan. 30, 2002, the entire disclosure of which is hereby incorporated by reference.

FIELD OF THE INVENTION

The present invention relates to an iron oxide based catalyst and to a process for the preparation of the catalyst. The present invention also relates to a process for the dehydrogenation of an alkylaromatic compound which process comprises contacting a feed comprising the alkylaromatic compound with the catalyst of this invention.

BACKGROUND OF THE INVENTION

Iron oxide based catalysts are used in the dehydrogenation of an alkylaromatic compound to yield, as the desired, main product, the corresponding alkenylaromatic compound.

However, when using the iron oxide based catalysts in the dehydrogenation of alkylaromatic compounds, several side reactions occur which decrease the yield of alkenylaromatic compound and therefore effect the economy of the process unfavorably. One such side reaction is the formation of coke on the catalyst, which reduces the lifetime of the catalyst. Other side reactions involve the formation of an alkynylaromatic compound, a methylaromatic compound, and a dealkylated aromatic compound. For example, in the dehydrogenation of ethylbenzene, the desired, main product is styrene and undesired byproducts are coke, phenylacetylene, toluene and benzene.

In view of the applicability and use of the alkenylaromatic compound, the alkynylaromatic compound is frequently at least partly removed from the product of the dehydrogenation. This removal generally requires a separate process step, typically involving hydrogenation to the alkenylaromatic compound, using a selective hydrogenation catalyst.

U.S. Pat. No. 5,190,906 and EP-A-1027928 disclose that the source of the iron oxide for use in the iron oxide catalysts may be a process which comprises heat decomposition of an iron halide. By nature, such iron oxide catalysts produced by heat decomposition of an iron halide contain residual iron halide.

For example, dehydrogenation catalysts are in commercial use for the dehydrogenation of an alkylaromatic compound, which catalysts are based on an iron oxide made by heat decomposition of an iron halide, and further contain a small amount of a lanthanide, for example 0.066 mole per mole of iron oxide, calculated as $Fe_2O_3$.

When in the dehydrogenation of an alkylaromatic compound such commercially available catalysts are applied alkynylaromatic compound is co-produced. It would be highly desirable to decrease the selectivity to the co-produced alkynylaromatic compound. As used herein, the selectivity to a particular compound means the fraction of the converted alkylaromatic compound yielding the particular compound.

SUMMARY OF THE INVENTION

When using a catalyst which is based on an iron oxide obtained from iron halide heat decomposition and which contain halide by nature the selectivity to the alkynylaromatic compound is reduced, if the catalyst comprises, as described herein, a defined quantity of a lanthanide.

This result is non-obvious, as a similar presence of a lanthanide in catalysts which are based on an iron oxide of another source does not significantly cause the selectivity to alkynylaromatic compound to decrease. The prior art documents acknowledged hereinbefore are silent as regards the particular influence of the lanthanide on the selectivity to alkynylaromatic compounds, which apparently depends on the iron oxide in respect of its source and/or the presence of halide.

Accordingly, the present invention provides a catalyst which is based upon an iron oxide and a compound of a lanthanide, of which iron oxide at least a portion is made by a process which comprises heat decomposition of an iron halide, and which catalyst comprises the lanthanide in a quantity of from 0.07 to 0.15 mole per mole iron oxide present in the catalyst, calculated as $Fe_2O_3$.

The present invention also provides a catalyst which is based upon an iron oxide and a compound of a lanthanide, of which iron oxide at least a portion has a residual halide content, and which catalyst comprises the lanthanide in a quantity of from 0.07 to 0.15 mole per mole iron oxide present in the catalyst, calculated as $Fe_2O_3$. In this embodiment, the residual halide content is in particular in the range of from 10 to 3000 parts per million by weight (ppmw), more in particular from 50 to 2000 ppmw, calculated as the weight of halogen relative to the weight of the said portion of the iron oxide.

The present invention also provides a process for the preparation of a catalyst comprising iron oxide and a lanthanide in a quantity of from 0.07 to 0.15 mole per mole iron oxide present in the catalyst, calculated as $Fe_2O_3$, which process comprises preparing a mixture comprising an iron oxide and a compound of the lanthanide, and claiming the mixture, wherein at least a portion of the iron oxide is made by a process which comprises heat decomposition of an iron halide.

The present invention further provides a process for the preparation of a catalyst comprising iron oxide and a lanthanide in a quantity of from 0.07 to 0.15 mole per mole iron oxide present in the catalyst, calculated as $Fe_2O_3$, which process comprises preparing a mixture comprising an iron oxide and a compound of the lanthanide, and claiming the mixture, wherein at least a portion of the iron oxide has a residual halide content, in particular in the range of from 10 to 3000 ppmw, more in particular from 50 to 2000 ppmw, calculated as the weight of halogen relative to the weight of the said portion of the iron oxide.

The present invention further provides a process for the dehydrogenation of an alkylaromatic compound which process comprises contacting a feed comprising the alkylaromatic compound with a catalyst according to this invention.

The present invention further provides a method of using an alkenylaromatic compound for making polymers or copolymers, comprising polymerizing the alchemy aromatic compound to form a polymer or copolymer comprising monomer units derived from the alkenylaromatic compound, wherein the alkenylaromatic compound has been prepared in a process for the dehydrogenation of an alkylaromatic compound according to this invention.

DETAILED DESCRIPTION OF THE INVENTION

As used herein, unless defined otherwise, the quantity of metal components in the catalysts and precursor mixtures, other than the iron components, is expressed as the number of moles of the metal relative to the total number of moles of iron oxide present in the catalyst, calculated as $Fe_2O_3$.

The catalysts of this invention are based upon iron oxide which is obtained by heat decomposition of an iron halide, optionally applying an oxidizing atmosphere wherein iron(II) is oxidized to iron(III). The halide may comprise a chloride and/or a bromide. Typically, the iron halide comprises iron dichloride, in particular iron dichloride. Heat decomposition may comprise spray roasting wherein an iron halide solution is sprayed from nozzles into a directly heated reaction chamber, as disclosed in U.S. Pat. No. 5,911,967, which is herein incorporated by reference. Alternative heat decomposition methods utilize the iron halide as a gas or as a solid. Typically, the iron halide solution is a so-called waste pickle liquor. The iron oxide which is obtained by heat decomposition of the iron halide product may or may not be further treated, to decrease the iron halide content, before it is use in the present invention. Suitable treating methods are disclosed in U.S. Pat. No. 5,401,485 and U.S. Pat. No. 5,597,547, which are incorporated herein by reference.

The iron oxide obtained by heat decomposition of an iron halide as used in the present invention may typically have a residual halide content of less than 3000 ppmw, more typically less than 2000 ppmw, in particular less than 1500 ppmw, calculated as the weight of halogen relative to the weight of the iron oxide. Generally, it is preferred that the residual halide content is low. On the other hand, when practicing the present invention, the residual halide may frequently be above 10 ppmw, more frequently above 50 ppmw, calculated as the weight of halogen relative to the weight of the iron oxide.

A preferred catalyst can be obtained by combining yellow iron oxide with the iron oxide which is obtained by heat decomposition of an iron halide. The skilled person is aware that yellow iron oxide is a hydrated iron oxide, frequently depicted as $\alpha$-FeOOH or $Fe_2O_3 \cdot H_2O$. The yellow iron oxide may suitably be applied in a quantity of up to 50%w, calculated as the weight of $Fe_2O_3$ relative to the total weight of iron oxide, as $Fe_2O_3$, present in the catalyst. Preferably, the yellow iron oxide is applied in a quantity of at least 1%w, in particular from 5 to 30%w, on the same basis, for example, 8.8%w, 10%w, 15%w, 17%w or 20%w.

Minor amounts of other iron oxides or iron oxide-providing compounds may be combined with the iron oxide which is obtained by heat decomposition of an iron halide, but that is generally not preferred. Examples of such other iron oxides are black and red iron oxides. An example of a red iron oxide is so-called Penniman red iron oxide, i.e. iron oxide made by the Penniman method, for example as disclosed in U.S. Pat. No. 1,368,748. Examples of iron oxide-providing compounds include goethite, hematite, magnetite, magnetite, lepidocricite and mixtures thereof.

Generally, it is preferred that the quantity of the iron oxide which is obtained by heat decomposition of an iron halide is at least 50%w, particular at least 70%w, up to 100%w, calculated as $Fe_2O_3$ relative to the total weight of iron oxide, as $Fe_2O_3$, present in the catalyst.

The lanthanide is typically a lanthanide of atomic number in the range of from 57 to 66 (inclusive). Preferably the lanthanide is lanthanum or, in particular, cerium. The lanthanide is typically applied in a quantity of at least 0.08 mole, in-particular at least 0.1 mole, per mole iron oxide. The lanthanide is typically applied in a total quantity of at most 0.15 mole, more typically at most 0.14 mole, per mole iron oxide, as this tends to improve the overall selectivity to the desired alkenylaromatic compound. For example, the lanthanide may be applied in a quantity of 0.09 mole, or 0.113 mole, or 0.116 mole, or 0.12 mole, or 0.122 mole, or 0.123 mole, or 0.126 mole, or 0.15 mole, per mole iron oxide.

Typically, one or more compounds of molybdenum, tungsten, vanadium, copper and/or chromium may be present in the catalyst, as an additional component. Compounds of these metals tend to increase the dehydrogenation activity of the catalyst. In preferred embodiments tungsten or, in particular, molybdenum may be applied. The total quantity of one or more of molybdenum, tungsten, vanadium, copper and chromium may typically be at least 0.001 mole, more typically at least 0.005 mole, per mole iron oxide. Typically the total quantity is at most 0.1 mole, more typically at most 0.05 mol, in particular at most 0.02 mol, per mole iron oxide. For example, tungsten may be applied in a quantity of 0.0075 mole, or 0.0135 mole, or 0.0275 mole, per mole iron oxide; molybdenum may be applied in a quantity of 0.011 mole, or 0.018 mole, or 0.019 mole, per mole iron oxide; chromium may be applied in a quantity of 0.0085 mole, or 0.035 mole, per mole iron oxide; vanadium may be applied in a quantity of 0.01 mole, or 0.043 mole, or 0.045 mole, or 0.046 mole, or 0.047 mole, per mole iron oxide; and copper may be applied in a quantity of 0.006 mole, or 0.081 mole, per mole iron oxide.

Typically, one or more compounds of an alkali metal may be present in the catalyst, as an additional component. Compounds of these metals tend to diminish the deposition of coke on the catalyst during the dehydrogenation, and thereby tend to increase the lifetime of the catalyst. They also tend to increase the selectivity to the desired alkenylaromatic compound. In preferred embodiments, the alkali metal is cesium or rubidium, or, in particular, potassium. The alkali metals may be applied typically in a total quantity of at least 0.2 mole, more typically at least 0.25 mole, in particular at least 0.3 mole, more in particular at least 0.45 mole, most in particular at least 0.55 mole, per mole iron oxide, and typically in a quantity of at most 5 mole, more typically at most 1 mole, per mole iron oxide. For example, the alkali metals may be applied in a total quantity of 0.525 mole, 0.534 mole, or 0.575 mole, or 0.615 mole, or 0.623 mole, or 0.629 mole, or 0.643 mole, or 0.85 mole, per mole iron oxide.

Typically, one or more compounds of an alkaline earth metal may be present in the catalyst, as an additional component. Compounds of these metals tend to increase the selectivity to the desired alkenylaromatic compound, and to decrease the rate of decline of the catalyst activity. In preferred embodiments, the alkaline earth metal is magnesium or, in particular, calcium. The alkaline earth metals may be applied typically in a quantity of at least 0.01 mole, more typically at least 0.02 mole, in particular at least 0.03 mole, per mole of iron oxide, and typically in a total quantity of at most 1 mole, more typically at most 0.2 mole, in particular at most 0.13 mole, more in particular at most 0.1 mole, per mole of iron oxide. For example, the alkaline earth metals may be applied in a total quantity of 0.025 mole, or 0.026 mole, or 0.075 mole, or 0.076 mole, or 0.078 mole, or 0.079 mole, or 0.138 mole, or 0.14 mole, per mole of iron oxide.

It is not material to the invention which kind of lanthanide, molybdenum, tungsten, chromium, copper, vanadium, alkali metal or alkaline earth metal compounds are applied. Suitably, these metal compounds may, independently, be selected from hydroxides; bicarbonates; carbonates; carboxylates, for example formats, acetates, oxalates and citrates; nitrates; oxides; jollyboats; Tung states; chromates; and van dates. Oxygenated compounds like jollyboats; Tung states; chromates; and van dates may be employed as the acid, or as a suitable salt, such as the potassium, calcium, magnesium or any ammonium salt. The carboxylates are typically derived from carboxylic acids having up to 10 carbon atoms, inclusive, more typically from 1 to 6 carbon atoms, inclusive. More in general, after the calcinations the metal compounds are typically present in the catalysts as the corresponding metal oxides and it is therefore preferred that the metal compounds applied are suitable metal oxide precursors.

The methods by which the catalysts may be prepared are not material to the invention. Typically, the catalyst may be prepared by preparing a mixture of the iron oxide(s) and any further component(s), such as any metal compound referred to above, in a sufficient quantity and claiming the mixture. Sufficient quantities may be calculated from the composition of the catalyst to be prepared. Examples of applicable methods can be found in U.S. Pat. No. 5,689,023, U.S. Pat. No. 5,171,914, U.S. Pat. No. 5,190,906, U.S. Pat. No. B1-6,191,065, and EP-A-1027928, which are herein incorporated by reference.

Before calcinations, the mixture may be shaped into pellets of any suitable form, such as tablets, spheres, pills, saddles, triodes, tetra lobes, rings, stars, and hollow and solid cylinders. The addition of a suitable quantity of water, for example up to 30% w, typically from 2 to 20% w, calculated on the weight of the mixture, may facilitate the shaping into pellets. If water is added, it may be removed at least partly prior to calcinations. Suitable shaping methods are pelletizing, extrusion, pressing, spraying and spray drying. If desired, spray drying may be extended to include the calcinations.

A shaping aid, or extrusion aid, may be applied, for example a saturated or unsaturated fatty acid (such as politic acid, satiric acid or oleic acid) or a salt thereof, a polysaccharide derived acid or a salt thereof, or graphite, starch, or cellulose. Any salt of a fatty acid or polysaccharide derived acid may be applied, for example an ammonium salt or a salt of any metal mentioned hereinbefore. The fatty acid may comprise from 6 to 30 carbon atoms (inclusive), preferably from 10 to 25 carbon atoms (inclusive). When a fatty acid or a polysaccharide derived acid is used, it may combine with a metal salt applied in preparing the catalyst, to form a salt of the fatty acid or polysaccharide derived acid. A suitable quantity of the shaping or extrusion aid is, for example, up to 1%w, in particular 0.001 to 0.5%w, relative to the weight of the mixture to be shaped.

The calcinations comprises heating the mixture, typically in an inert or oxidizing atmosphere, for example in nitrogen, helium, or an oxygen containing gas, such as air, oxygen enriched air or an oxygen/inert gas mixture. The calcinations temperature is typically at least 600° C., preferably at least 700° C. It has been found that when the calcinations is carried out at a higher temperature, the catalyst exhibits, advantageously, an increased selectivity to the formation of alkenylaromatic compound. When practicing the present invention, the calcinations temperature will suitably be at most 1200° C., more suitably at most 1100° C. For example, the calcinations may be carried out at 725° C., or 767° C., or 845° C., or 860° C., or 921° C., or 925° C., or 950° C. Typically the duration of calcinations is from 5 minutes to 12 hours, more typically from 10 minutes to 6 hours, for example 15 minutes, or 1.5 hours, or 3 hours, or 5 hours.

The surface structure of the catalyst, typically in terms of pore volume, median pore diameter and surface area, may be chosen within wide limits. The skilled person is aware that he can influence the surface structure by the selection of the temperature and time of calcinations, and by the application of an extrusion aid.

Suitably, the pore volume is at least 0.01 ml/g, more suitably at least 0.05 ml/g. Suitably, the pore volume is at most 0.5, preferably less than 0.2, in particular at most 0.18 ml/g, more in particular at most 0.16 ml/g. For example, the pore volume may be 0.118 ml/g, or 0.122 ml/g, or 0.143 ml/g.

Suitably, the median pore diameter is at least 500 A, in particular at least 1000 Å. Suitably, the median pore diameter is at most 5000 Å, in particular less than 3000 Å. In a preferred embodiment, the median pore diameter is in the range of from 1200 to 2800 Å. For example, the median pore diameter may be 1360 Å, or 2080 Å, or 2670 Å. As used herein, the pore volumes and median pore diameters are as measured by mercury intrusion according to ASTM D4282-92, to an absolute pressure of 6000 psia ($4.2 \times 10^7$ Pa using a Micromeretics Auto pore 9420 model (1300 contact angle, mercury with a surface tension of 0.473 N/m). As used herein, median pore diameter is defined as the pore diameter at which 50% of the mercury intrusion volume is reached.

The surface area of the catalyst is suitably in the range of from 0.01 to 20 $m^2/g$, more suitably from 0.1 to 10 $m^2/g$, for example 2.6 $m^2/g$, or 3.4 $m^2/g$, or 4.9 $m^2/g$, or 5 $m^2/g$. As used herein, surface area is understood to refer to the surface area as determined by the BET (Brunauer, Emmett and Teller) method as described in Journal of the American Chemical Society 60 (1938) pp. 309-316.

The crush strength of the catalyst is suitably at least 10 N/mm, and more suitably it is in the range of from 20 to 100 N/mm, for example about 55 or 60 N/mm.

The present process for preparing an alkenylaromatic compound (hereinafter referred to as "the dehydrogenation process") comprises contacting the feed comprising the alkylaromatic compound with the catalyst of this invention. The dehydrogenation process is frequently a gas phase process, wherein a gaseous feed comprising the reactants is contacted with the solid catalyst. The catalyst is suitably present in the form of a fluidized bed of catalyst particles, or, more suitable, in the form of a packed bed. The process may be carried out as a batch process. However, it is more suitable to carry out the dehydrogenation process as a continuous process. The skilled person will appreciate that hydrogen is a further product of the dehydrogenation process, and that the dehydrogenation in question is a non-oxidative dehydrogenation. Examples of applicable methods for carrying out the dehydrogenation process can be found in U.S. Pat. No. 5,689,023, U.S. Pat. No. 5,171,914, U.S. Pat. No. 5,190,906, U.S. Pat. No. B1-6,191,065, and EP-A-1027928, which are herein incorporated by reference.

The alkylaromatic compound is typically an alkyl substituted benzene, although other aromatic compounds may be applied as well, such as an alkyl substituted naphthalene, anthracite or pyridine. The alkyl substituent may have any carbon number of two and more, for example, up to 6, inclusive. Suitable alkyl substituent's are propel ($—CH_2—CH_2—CH_3$), 2-propel (i.e. 1methyl ethyl, $—CH(—CH_3)_2$), butyl ($—CH_2—CH_2—CH_2—CH_3$), 2methyl-propel ($—CH_2—CH(—CH_3)2$), and hexyls ($—CH_2—CH_2—CH_2—CH_2—CH_2—CH_3$), in particular ethyl ($—CH_2—CH_3$). Examples of suitable alkylaromatic compounds are butyl benzene, hexylbenzene, (2-methylpropyl)benzene, (1methyl ethyl)benzene (i.e. cymene), l-ethyl-2-methylbenzene, 1,4-diethyl benzene, in particular methylbenzene.

It is advantageous to apply water, preferably in the form of steam, as an additional component of the feed. The presence of water will decrease the rate of deposition of coke on the catalyst during the dehydrogenation process. Typically the molar ratio of water to the alkylaromatic compound in the feed is in the range of from 1 to 50, more typically from 3 to 30, for example 5 or 10.

The dehydrogenation process is typically carried out at a temperature in the range of from 500 to 700° C., more typically from 550 to 650° C., for example 600° C., or 630° C. In an embodiment, the dehydrogenation process is carried out isothermally. In other embodiments, the dehydrogenation process is carried out in an adiabatic manner, in which case the temperatures mentioned are reactor inlet temperatures, and as the dehydrogenation progresses the temperature may decrease typically by up to 150° C., more typically by from 10 to 120° C. The absolute pressure is typically in the range of from 10 to 300 kPa, more typically from 20 to 200 kPa, for example 50 kPa, or 120 kPa.

If desired, one, two or more reactors, for example three or four, may be applied. The reactors may be operated in series or parallel. They may or may not be operated independently from each other, and each reactor may be operated under the same conditions or under different conditions.

When operating the dehydrogenation process as a gas phase process using a packed bed reactor, the LHSV may preferably be in the range of from 0.01 to 10/(l.h), more preferably in the range of from 0.1 to 2/(l.h). As used herein, the term "LHSV" stands for the Liquid Hourly Space Velocity, which is the liquid volumetric flow rate of the hydrocarbon feed, measured at normal conditions (i.e. 0° C. and 1 bar absolute), divided by the volume of the catalyst bed, or by the total volume of the catalyst beds if there are two or more catalyst beds.

In preferred embodiments the conditions of the dehydrogenation process are selected such that the conversion of the alkylaromatic compound is in the range of from 30 to 80 mole-%, more preferably in the range of from 35 to 75 mole-%, for example 40 mole-%, or 67 mole-%.

The alkenylaromatic compound may be recovered from the product of the dehydrogenation process by any known means. For example, the dehydrogenation process may include a fractional distillation or reactive distillation. If desirable, the dehydrogenation process may include a hydrogenation step in which at least a portion of the product is subjected to hydrogenation by which at least a portion of the alkynylaromatic compound, if any is present, is converted into the alkenylaromatic compound. The portion of the product subjected to hydrogenation may be a portion of the product which is enriched in the alkynylaromatic compound. Such hydrogenation is known in the art. For example, the methods known from U.S. Pat. No. 5,504,268, U.S. Pat. No. 5,156,816 U.S. Pat. No. 4,822,936, which are incorporated herein by reference, are readily applicable to the present invention.

It is an unexpected benefit of the present invention that the quantity of alkynylaromatic compound present in the dehydrogenation product, if any, is lower than without practicing the invention, so that there is less need to apply the hydrogenation step, or the hydrogenation step may be carried out with less catalyst relative to the feed, or under milder conditions. It is also an unexpected benefit of the invention that an improved activity for a given selectivity or an improved selectivity for a given activity is obtained in the dehydrogenation, in particular when the alkali metal is employed at a relatively high quantity, for example at least 0.45 mole, in particular at least 0.55 mole, per mole iron oxide, preferably in combination with a high quantity of the lanthanide, for example at least 0.07 mole, in particular at least 0.1 mole, per mole iron oxide. Such catalysts tend to provide, in addition, an improved stability when operated in a dehydrogenation process wherein the molar ratio of water to the alkylaromatic compound is low, for example below 10, in particular at most 7.

The alkenylaromatic compound produced by the dehydrogenation process of this invention may be used as a monomer in polymerization processes and copolymerization processes. For example, the styrene obtained may be used in the production of polystyrene, styrene/dyne rubbers and the like. The improved catalyst performance achieved by this invention leads to a more attractive process for the production of the alkenylaromatic compound and concurrently to a more attractive process which comprises producing the alkenylaromatic compound and the subsequent use of the obtained alkenylaromatic compound in the manufacture of polymers and copolymers which comprise monomer units of the alkenylaromatic compound. For applicable polymerization catalysts, polymerization processes, polymer processing methods and uses of the resulting polymers, reference is made to H F Marks, et al. (Ed.), "Encyclopedia of Polymer Science and Engineering", $2^{nd}$ Edition, New York, Volume 16, pp. 1-246, and the references cited therein, which is/are incorporated herein by reference.

The invention will be illustrated by means of the following, non-limiting examples.

EXAMPLE 1

A paste was made by mixing the following ingredients: iron oxide made by heat decomposition of an iron halide (Hoogovens Regenerated iron oxide, type RIO250), yellow iron oxide (Bayer, type 920Z), cerium carbonate, potassium carbonate, molybdenum trioxide, calcium carbonate, and water (about 10% w, relative to the weight of the dry mixture). The paste was extruded to form 3-mm diameter cylinders cut into 6-mm lengths. The pellets were dried in air at 170° C. for 15 hours and subsequently claimed in air at 825° C. for 1 hours. After calcinations, the composition of the catalyst was, per mole iron oxide, 0.615 mole potassium, 0.12 mole cerium, 0.0175 mole molybdenum, 0.025 mole calcium, all per mole of iron oxide, as $Fe_2O_3$, present. The quantity of yellow iron oxide was 8.8%, as $Fe_2O_3$, relative to the total quantity (number of moles) of iron oxide, as $Fe_2O_3$, present in the catalyst.

Three samples of the catalyst were used for the preparation of styrene from methylbenzene under isothermal testing conditions in a reactor designed for continuous operation. The samples were used in three separate tests. In each test the conditions were as follows: absolute pressure 76 kPa, steam to methylbenzene molar ratio 10, LHSV 0.65 l/l.h. In each test stable conditions were reached after 400 hours, and the temperatures were selected such that in each test a 70%mole conversion of methylbenzene was achieved. In the three tests, the temperatures were 584.4° C., 582.6° C., and 584.6° C., i.e. on average 583.9° C. The selectivity to styrene was on average 94.4%mole.

Three samples of the catalyst were used for the preparation of styrene from methylbenzene in three separate tests, as described in the previous paragraph, with the differences that the steam to methylbenzene molar ratio 5, instead of 10, and the absolute pressure was lowered from 76 kPa to 40 kPa. In the three tests, the temperatures were 596.8° C., 597.4° C., and 596.8° C., i.e. on average 597.0° C. The selectivity to styrene was on average 96.2% mole.

EXAMPLE 2

A first experimental design was set-up and executed in accordance with the experimental procedures as described in Example 1. The experimental design covered variations in the quantities of potassium: 0.515, 0.565 and 0.615 mole/mole $Fe_2O_3$,
calcium: 0.025, 0.050 and 0.075 mole/mole $Fe_2O_3$,
cerium: 0.050, 0.085 and 0.120 mole/mole $Fe_2O_3$,
molybdenum: 0.005, 0.0175 and 0.030 mole/mole $Fe_2O_3$,
copper: 0, 0.050 and 0.100 mole/mole $Fe_2O_3$, chromium: 0, 0.050 and 0.100 mole/mole $Fe_2O_3$, and
yellow iron oxide: 0, 10 and 20% w, relative to the total quantity of iron oxide; and in
the calcinations temperature: 725, 825 and 925° C.

The effects on the preparation of styrene from methylbenzene were examined. It was found that an increase of the quantity of cerium provides a significant decrease of the selectivity to phenyl acetylene.

Confirmation of this result was found by setting-up and executing a second experimental design which differed from the first in that molybdenum was present in a fixed quantity of 0.0175 mole/mole $Fe_2O_3$, and that no copper and chromium were present.

For comparative purposes, a similar experimental design was set-up and executed, wherein a Penniman red iron oxide was used instead of iron oxide made by heat decomposition of an iron halide. This experimental design covered variations in the quantities of calcium: 0.025, 0.075 and 0.125 mole/mole $Fe_2O_3$,
cerium: 0.050, 0.075 and 0.100 mole/mole $Fe_2O_3$, and
molybdenum: 0.010, 0.030 and 0.050 mole/mole $Fe_2O_3$).

The quantity of potassium was 0.550 mole/mole $Fe_2O_3$, no copper and chromium were present and the calcinations temperature was 825° C. It was found that an increase of the quantity of cerium does not provide a significant decrease of the selectivity to phenyl acetylene.

What is claimed is:

1. A catalyst comprising an iron oxide component and a compound of a lanthanide, wherein said iron oxide component is made by a process which comprises heat decomposition of an iron halide, wherein said lanthanide is present in said catalyst in a quantity in the range of from 0.07 to 0.15 mole per mole iron oxide present in said catalyst, calculated as $Fe_2O_3$, said iron oxide component has a halide content of at least 10 parts per million by weight, and said catalyst has a median pore diameter of at most 5000 Å.

2. A catalyst as claimed in claim 1, wherein said iron oxide component has a halide content of from 10 to 3000 parts per million by weight.

3. A catalyst as claimed in claim 2, wherein said iron oxide component has a halide content of from 50 to 2000 parts per million by weight.

4. A catalyst as claimed in claim 1, wherein the lanthanide has an atomic number in the range of from 57 to 66 (inclusive).

5. A catalyst as claimed in claim 4, wherein the lanthanide compound is cerium.

6. A catalyst as claimed in claim 1, further comprising a compounds of an alkali metal present in said catalyst in a total quantity of at least 0.45 mole per mole iron oxide present in the catalyst, calculated as $Fe_2O_3$.

7. A catalyst as claimed in claim 6, wherein the catalyst comprises the alkali metal in a total quantity in the range of from 0.55 to 5 mole per mole iron oxide present in the catalyst, calculated as $Fe_2O_3$.

8. A catalyst as claimed in claim 6, wherein the alkali metal is potassium.

9. A catalyst as claimed in claim 1, further comprising a compound of an alkaline earth metal present in said catalyst in a total quantity in the range of from 0.01 to 0.2 mole per mole iron oxide present in the catalyst, calculated as $Fe_2O_3$.

10. A catalyst as claimed in claim 9, wherein the catalyst comprises the alkaline earth metal in a total quantity in the range of 0.02 to 0.13 mole per mole iron oxide present in the catalyst, calculated as $Fe_2O_3$.

11. A catalyst as claimed in claim 9, wherein the alkaline earth metal is selected from the group consisting of calcium, magnesium, and a combination thereof.

12. A catalyst as claimed in claim 1, further comprising an additional component selected from the group consisting of compounds of molybdenum, compounds of tungsten, compounds of vanadium, and compounds of chromium, wherein said additional component is present in said catalyst in a total quantity in the range of from 0.001 to 0.1 mole per mole iron oxide present in the catalyst, calculated as $Fe_2O_3$.

13. A catalyst as claimed in claim 12, wherein the catalyst comprises said additional component in a total quantity in the range of from 0.005 to 0.05 mole per mole iron oxide present in the catalyst, calculated as $Fe_2O_3$.

14. A catalyst as claimed in claim 12, wherein said additional component is a compound of molybdenum or a compound of tungsten, or both.

15. A catalyst as claimed in claim 1, wherein the catalyst has a median pore diameter of less than 3000 Å.

16. A catalyst as claimed in claim 15, wherein the catalyst has a median pore diameter in the range of from 1200 to 2800 Å.

17. A catalyst as claimed in claim 1, wherein the catalyst includes a yellow iron oxide.

18. A catalyst as claimed in claim 17, wherein the yellow iron oxide is applied in a quantity of up to 50% wt., calculated as the weight of $Fe_2O_3$ relative to the total weight of iron oxide, as $Fe_2O_3$, present in the catalyst.

19. A catalyst as claimed in claim 18, wherein the yellow iron oxide is applied in a quantity in the range of from 1 to 30 % wt., calculated as the weight of $Fe_2O_3$ relative to the total weight of iron oxide, as $Fe_2O_3$, present in the catalyst.

20. A catalyst as claimed in claim 1, wherein the catalyst further comprises a compound of an alkali metal, a compound of an alkaline earth metal, and an additional compound selected from the group consisting of compounds of molybdenum, compounds of tungsten, compounds of vanadium compounds of chromium, and combinations thereof which said catalyst comprises the alkali metal in a total quantity of at least 0.45 mole per mole iron oxide present in the catalyst, calculated as $Fe_2O_3$, the alkaline earth metal in a total quantity in the range of from 0.01 to 0.2 mole per mole iron oxide present in the catalyst, calculated as $Fe_2O_3$, and said additional compound in a total quantity in the range of from 0.001 to 0.1 mole per mole iron oxide present in the catalyst, calculated as $Fe_2O_3$.

21. A catalyst as claimed in claim 20, wherein the catalyst further comprises yellow iron oxide present in a quantity of in the range of from 1 to 30 % wt., calculated as the weight of $Fe_2O_3$ relative to the total weight of iron oxide, as $Fe_2O_3$, present in the catalyst.

22. A catalyst comprising an iron oxide component and a compound of a lanthanide, wherein said iron oxide component contains a residual halide content, and which catalyst comprises the lanthanide in a quantity of from 0.07 to 0.15 mole per mole iron oxide present in the catalyst, calculated as $Fe_2O_3$, and wherein said catalyst has a median pore diameter of at most 5000 Å.

23. A catalyst as claimed in claim 22, wherein the residual halide content is in the range of from 10 to 3000 parts per million by weight, calculated as the weight of halogen relative to the weight of said iron oxide component.

24. A catalyst as claimed in claim 23, wherein the residual halide content is in the range of from 50 to 2000 parts per million by weight, calculated as the weight of halogen relative to the weight of the said iron oxide component.

25. A catalyst as claimed in claim 22, wherein the catalyst further comprises a compound of an alkali metal, a compound of an alkaline earth metal, and an additional compound selected from the group consisting of compounds of molybdenum, compounds of tungsten, compounds of vanadium, compounds of chromium and mixtures thereof, which catalyst comprises the alkali metal in a total quantity of at least 0.45 mole per mole iron oxide present in the catalyst, calculated as $Fe_2O_3$, the alkaline earth metal in a total quantity in the range of from 0.01 to 0.2 mole per mole iron oxide present in the catalyst, calculated as $Fe_2O_3$, and the additional compound in a total quantity in the range of from 0.001 to 0.1 mole per mole iron oxide present in the catalyst, calculated as $Fe_2O_3$.

26. A process for the preparation of a catalyst as claimed in claim 1, which process comprises preparing a mixture comprising sufficient quantities of at least the iron oxide and the compound of the lanthanide, and calcining the mixture to form the catalyst.

27. A process as claimed in claim 26, wherein the temperature of calcination is in the range of from 600 to 1200° C.

28. A process as claimed in claim 27, wherein the temperature of calcination is in the range of from 700 to 1100° C.

29. A process for the preparation of a catalyst as claimed in claim 20, which process comprises preparing a mixture comprising sufficient quantities of at least the iron oxide, the compound of the lanthanide, one or more compounds of an alkali metal, one or more compounds of an alkaline earth metal, and one or more compounds of molybdenum, tungsten, vanadium and/or chromium, and calcining the mixture to form the catalyst.

30. A process as claimed in claim 29, wherein the temperature of calcination is in the range of from 600 to 1200° C.

31. A process as claimed in claim 30, wherein the temperature of calcination is in the range of from 700 to 1100° C.

32. A process for the preparation of a catalyst as claimed in claim 21, which process comprises preparing a mixture comprising sufficient quantities of at least the iron oxides, one or more compounds of the lanthanide, one or more compounds of an alkali metal, one or more compounds of an alkaline earth metal, and one or more compounds of molybdenum, tungsten, vanadium and/or chromium, and calcining the mixture to form the catalyst.

33. A process for the preparation of a catalyst as claimed in claim 22, which process comprises preparing a mixture comprising sufficient quantities of at least the iron oxide and the compound of the lanthanide, and calcining the mixture to form the catalyst.

34. A process as claimed in claim 33, wherein the temperature of calcination is in the range of from 600 to 1200° C.

35. A process as claimed in claim 34, wherein the temperature of calcination is in the range of from 700 to 1100° C.

36. A process for the preparation of a catalyst as claimed in claim 25, which process comprises preparing a mixture comprising sufficient quantities of at least the iron oxide, one or more compounds of the lanthanide, one or more compounds of an alkali metal, one or more compounds of an alkaline earth metal, and one or more compounds of molybdenum, tungsten, vanadium and/or chromium, and calcining the mixture to form the catalyst.

37. A process as claimed in claim 36, wherein the temperature of calcination is in the range of from 600 to 1200° C.

38. A process as claimed in claim 37, wherein the temperature of calcination is in the range of from 700 to 1100° C.

39. A catalyst as claimed in claim 1 wherein said lanthanide is present in said catalyst in a quantity in the range of from 0.08 to 0.15 mole per mole iron oxide present in said catalyst, calculated as $Fe_2O_3$.

40. A process for preparing a catalyst comprising preparing a mixture of an iron oxide made by heat decomposition of an iron halide and a lanthanide and calcining the mixture wherein the lanthanide is present in the catalyst in a quantity in the range of from 0.07 to 0.15 mole per mole of iron oxide present in the catalyst, calculated as $Fe_2O_3$.

\* \* \* \* \*